United States Patent
Tsu et al.

(10) Patent No.: US 10,278,904 B2
(45) Date of Patent: May 7, 2019

(54) POWDER FOR DENTAL POWDER BLASTING

(71) Applicant: Christopher Louis Tsu, Le Muids (CH)

(72) Inventors: Christopher Louis Tsu, Le Muids (CH); Josée Desjardins, Le Muids (CH)

(73) Assignee: Christopher Louis Tsu, Le Muids (CH)

( * ) Notice: Subject to any disclaimer, the term of this patent is extended or adjusted under 35 U.S.C. 154(b) by 0 days.

(21) Appl. No.: 14/346,376

(22) PCT Filed: Sep. 21, 2012

(86) PCT No.: PCT/EP2012/068713
§ 371 (c)(1),
(2) Date: Mar. 21, 2014

(87) PCT Pub. No.: WO2013/041711
PCT Pub. Date: Mar. 28, 2013

(65) Prior Publication Data
US 2014/0242552 A1 Aug. 28, 2014

(30) Foreign Application Priority Data

Sep. 23, 2011 (EP) .................................... 11182507
May 2, 2012 (EP) .................................... 12166428

(51) Int. Cl.
*A61K 8/02* (2006.01)
*A61K 8/34* (2006.01)
(Continued)

(52) U.S. Cl.
CPC ............ *A61K 8/0233* (2013.01); *A61C 3/025* (2013.01); *A61K 8/022* (2013.01); *A61K 8/0241* (2013.01);
(Continued)

(58) Field of Classification Search
CPC .. A61C 1/00; A61C 1/087; A61C 3/02; A61C 3/025; A61C 15/00; A61C 17/00;
(Continued)

(56) References Cited

U.S. PATENT DOCUMENTS 4,160,820 A * 7/1979 Wagenknecht .......... A61K 8/27
424/48
4,978,391 A * 12/1990 Jones ....................... A61C 7/12
106/35
(Continued)

FOREIGN PATENT DOCUMENTS

| JP | 2011 192244 A | 7/1999 |
| JP | 2003 226628 A | 8/2003 |
| WO | WO 2010/068359 | 6/2010 |

OTHER PUBLICATIONS

Remineralizing tooth paste recipe from http://wellnessmama.com/2500/remineralizing-toothpaste/ (2011).

*Primary Examiner* — Heidi M Eide
*Assistant Examiner* — Mirayda A Aponte
(74) *Attorney, Agent, or Firm* — Chalin A. Smith; Smith Patent, LLC

(57) ABSTRACT

The present invention relates to calcium carbonate particles, a powder mixture including such particles and a tooth cleaning method wherein the particles or powder mixture are used.

9 Claims, 4 Drawing Sheets

(51) Int. Cl.
  *A61Q 11/00* (2006.01)
  *A61K 8/19* (2006.01)
  *B24C 11/00* (2006.01)
  *A61C 3/025* (2006.01)
  *A61K 8/21* (2006.01)

(52) U.S. Cl.
  CPC ............... *A61K 8/19* (2013.01); *A61K 8/21* (2013.01); *A61K 8/345* (2013.01); *A61Q 11/00* (2013.01); *B24C 11/00* (2013.01); *A61K 2800/61* (2013.01)

(58) Field of Classification Search
  CPC ... A61C 17/005; A61C 19/063; A61C 19/066; A61C 8/022; A61K 6/00–6/10; A61K 8/00; A61K 8/18–8/21; A61K 8/0233; A61K 8/0241; A61K 8/19; A61K 8/345; A61K 2800/61; A61K 6/0032; A61K 6/083; A61Q 11/00; B24C 11/00; Y10T 428/29; Y10T 428/2982; Y10T 428/2991; C09D 5/185; C09D 5/18; C09K 21/14; C08K 3/32; C08L 83/04
  USPC ............... 433/80, 82, 84, 88, 89, 215, 216; 424/46, 49, 52, 401; 523/179, 115; 427/203, 212
  See application file for complete search history.

(56) References Cited

U.S. PATENT DOCUMENTS

| | | | |
|---|---|---|---|
| 6,485,304 | B2 | 11/2002 | Beerstecher et al. |
| 6,509,007 | B2* | 1/2003 | Rajaiah ............... A23G 4/02 424/53 |
| 2007/0025929 | A1* | 2/2007 | Mohanty ............... A61K 8/02 424/52 |
| 2007/0258910 | A1* | 11/2007 | Arola ............... A61K 33/06 424/46 |
| 2010/0015068 | A1* | 1/2010 | Karp et al. ............... 424/57 |
| 2010/0297576 | A1 | 11/2010 | Donnet et al. |

* cited by examiner

POWDER FOR DENTAL POWDER BLASTING

PRIORITY

This application corresponds to the national phase of International Application No. PCT/EP2012/068713 filed Sep. 21, 2012 which, in turn, claims priority to European Patent Application Nos. 11.182507.1 filed Sep. 23, 2011 and 12.166428.8 filed May 2, 2012, the contents of which are incorporated by reference herein in their entirety.

FIELD OF THE PRESENT INVENTION

The present invention relates to calcium carbonate particles, a powder mixture comprising said particles and a tooth cleaning method wherein the particles or powder mixture are used.

BACKGROUND OF THE INVENTION

Dental plaque adhering to tooth constitutes a problem in oral hygiene and aesthetics. Cleaning the tooth by a toothbrush is most common for removing dental plaque and other coloring matter. In addition to this, interdental brushes, froth, hand scaler, air scaler and ultrasonic scalers are used. Furthermore, in dentist's sand blasting an abradant is sprayed on a tooth using compressed air or compressed air and water. Sodium bicarbonate, calcium carbonate, calcium phosphate, alumina, etc. are suggested as abradant used for this sand blasting (JP 11192244).

When treating sensitive tooth surfaces, like root dentine or other less strongly mineralized tooth surfaces, with a powder-jet device, it is recommended using powders with a low density and a low mean particle size of not more than 45 μm (US 2010/0297576). This document suggests using a powder for powder blasting with a powder-jet device wherein said powder contains an alditol having a low mean grain size of no larger than 45 μm. However, this powder is suitable for soft cleaning only because of its low abrasivity.

A dental powder-jet device including powders for dental abrasion is disclosed in U.S. Pat. No. 6,485,304 B2.

JP 2003-226628 discloses particles which support a fluoride ion supply compound and which can be incorporated for example in a mouth wash, chewing gum or dentifrices, such as tooth paste. It is said that the particles advance and remain inside the lacuna rill which is a favorite site of caries. Thereby the generating of caries of a lacuna rill part are inhibited by operation of the fluoride ion which is gradually released from the particles over a long time.

KR 2001-045447 discloses calcium carbonate particles being surface modified using fluorides. It is said that the modified calcium carbonate has a high acid-resistance, whiteness, and sterilization required for fillers, coaters and sterilizers of papers, cosmetics, tooth paste and pigments.

A home-made remineralization tooth paste recipe is disclosed on the web page for Wellness Mama®. This tooth paste contains five parts calcium carbonate, one part diatomaceous earth, two parts baking powder, three parts xylitol, one part liquid castile soap and 3-5 parts coconut oil. The xylitol is said to be not completely necessary but keeps the tooth paste from tasting bitter.

JP 1119224 discloses an abrasive compound for dental sand blasts which comprises an alditol, such as xylitol. It is said that by the use of xylitol the quality of the abrasive compound can be improved in taste.

The known abrasive powders for dental powder blasting have the disadvantage that they only have an abrasive effect, i.e. their only purpose is to clean the tooth surface for example by removing dental plaque or other coloring matter. On the other hand the enamel layer of the tooth is constantly attacked for example by the salvia resulting in a possible loss in density and/or thickness of this layer. In fact it was found that this damaging effect can even be increased by common abrasive powders. There is therefore still a need for improving the known abrasive powders, for example such that their damaging effect on the density and/or thickness of the enamel layer is reduced. Preferably the abrasive powder should even have a beneficial effect on the tooth, such as remineralization, thereby increasing the density and/or thickness of the enamel layer.

SUMMARY OF THE INVENTION

Assuming that remineralization of tooth surfaces is desirable, the present inventors considered calcium carbonate particles to have advantages over the most commonly used sodium bicarbonate particles. However, the expected effect on the remineralization of tooth when using calcium carbonate instead of sodium bicarbonate in powder blasting was only low. The inventors therefore made further investigations and surprisingly found that if the calcium carbonate particles are at least partially coated with an alkali metal fluoride, the desired effect on the remineralization of tooth is attained.

Thus, the present invention relates to the use of calcium carbonate particles being at least partially coated with an alkali metal fluoride for dental powder blasting.

DETAILED DESCRIPTION OF THE PREFERRED EMBODIMENTS

Figure 1A:
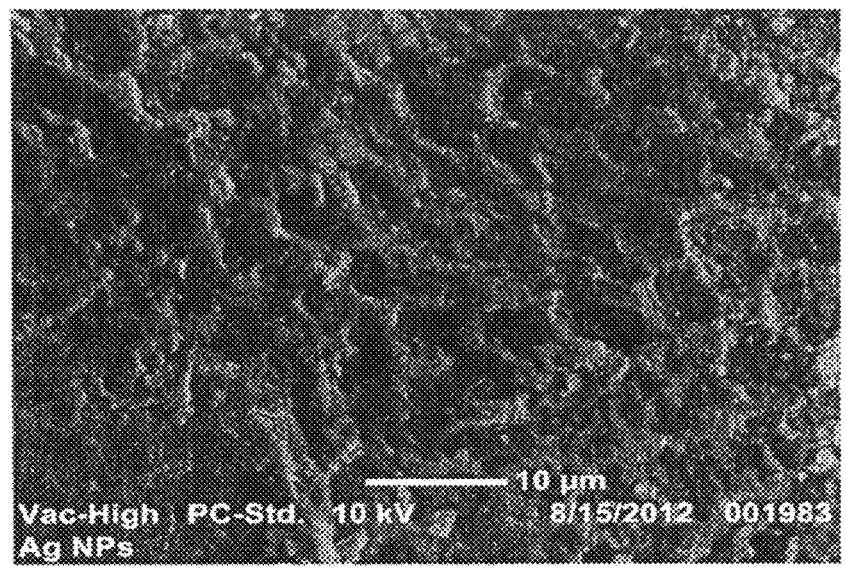
FIG. 1A is an image of demineralized bovine enamel before treatment with calcium carbonate in accordance with Example 2 (Group 1).

It was surprisingly found that the desired effect on the remineralization of tooth is not attained if calcium carbonate particles are only mixed with particles of the alkali metal fluoride. Only if the calcium carbonate particles are coated with the alkali metal fluoride the thus obtained particles help remineralization. While applicants do not wish to be bound to any theory it is believed that when the powder hits the tooth surface, it is in a slurry of water and the fluoride ion gets released immediately. A critical feature of the product to help remineralization is the speed of release. If this release is too slow, the calcium ions are already washed away and are thus no longer available for remineralization. Because of the coating of the calcium carbonate particles with the alkali metal fluoride, the fluoride ions get released into the patient's mouth immediately thereby facilitating remineralization of the tooth.

The alkali metal fluoride may preferably be selected from potassium fluoride and sodium fluoride. Most preferably the alkali metal fluoride is sodium fluoride.

The coating of the calcium carbonate particles with the alkali metal fluoride can be conducted by any suitable method known in the art. For example the calcium carbonate particles can be sprayed with a solution of the alkali metal fluoride. By evaporation of the solvent the alkali metal fluoride is deposited on the surface of the calcium carbonate particles forming the coating.

The size of the calcium carbonate particles is not particularly limited as long as they are suitable for the powder blasting of tooth surfaces. For example, the calcium carbonate particles may have a mean particle size in the range of about 10 µm to about 200 µm, preferably in the range of about 40 µm to about 100 µm, most preferably in the range of about 60 µm to about 70 µm, such as about 65 µm. The mean size of the particles is for example measured using the LS™ 13 320 Laser Diffraction Particle Size Analyzer available through Beckman Coulter, Inc. (Brea, Calif.).

In a preferred embodiment of the present invention the calcium carbonate particles have a narrow particle size distribution. Also preferred are calcium carbonate particles being substantially spherical.

The amount of alkali metal fluoride with which the calcium carbonate particles are coated can for example be in the range of about 1,000 ppm to about 20,000 ppm relative to the weight of the uncoated particles. Preferably, the calcium carbonate particles comprise an amount of alkali metal fluoride of about 1,000 ppm, about 1,500 ppm or about 12,300 ppm, each relative to the weight of the uncoated particles.

In further embodiments the present invention provides the use of calcium carbonate particles being at least partially coated with an alditol or being mixed with particles of at least one alditol for dental powder blasting. It has surprisingly been found that the presence of the alditol also facilitates the remineralization effect of the calcium carbonate particles.

In one embodiment the calcium carbonate particles used in one of the above described combinations with an alditol are those calcium carbonate particles being at least partially coated with an alkali metal fluoride as described above. In particular the particles have the same preferred features with respect to the alkali metal fluoride, the amount of the fluoride and their particle size as described above. The calcium carbonate particles being at least partially coated with the alkali metal fluoride may either be mixed with the particles of at least one alditol or they may be additionally at least partially be coated with the alditol. If the calcium carbonate particles are not coated with an alkali metal fluoride, they have nevertheless the above described preferred features with respect to for example particle size and particle size distribution.

As alditol for example mannitol, erythritol, xylitol and sorbitol are suitable. Xylitol is most preferred.

The mean size of the alditol particles should be selected such that it fits to the mean size of the calcium carbonate particles in that the mixture of the particles is physically stable, i.e. none of the particles separates from the mixture. Thus, the alditol particles suitably have a mean particle size in the range of about 10 µm to about 200 µm, preferably in the range of about 40 µm to about 100 µm, most preferably in the range of about 53 µm to about 88 µm. The mean particle size of the alditol particles is measured like the mean particle size of the calcium carbonate particles described above.

The amount of alditol added to the calcium carbonate particles either as coating or in a mixture is not particularly limited and can be selected by the skilled person according to the requirements. For example, the powder mixture can comprise from about 1 wt. % to about 20 wt. % of alditol, preferably from about 5 wt. % to about 15 wt. % of alditol, most preferably from about 7 wt. % to about 13 wt. % of alditol, each based on the total weight of the powder.

In a different embodiment of the present invention where the calcium carbonate particles are mixed with particles of at least one alditol the amount of alditol in the powder mixture may be higher, such as from about 50 wt. % to about 98 wt. %, preferably from about 70 wt. % to about 98 wt. %, more preferably from about 85 wt. % to about 95 wt. % of alditol particles, each based on the total weight of the powder.

It is suitable that the powder or powder mixture to be used for the dental powder blasting according to the invention substantially entirely or even entirely consists of the above described ingredients. Preferably the powder contains a maximum of about 20 wt. %, more preferably a maximum of about 10 wt. % and most preferably a maximum of about 2 wt. % of particles other than the calcium carbonate particles and the alditol particles, each based on the total weight of the powder. For example the powder may contain about 2 wt. % of silicone dioxide powder.

The above described calcium carbonate particles and the above described powder mixtures have the advantage of being not only suitable as cleaning powders abrasively removing some enamel during the cleaning process but they will clean and remineralize the tooth at the same time thereby protecting or even improving the enamel layer.

The present invention further relates to calcium carbonate particles being at least partially coated with an alkali metal fluoride and an alditol. A further embodiment relates to calcium carbonate particles being at least partially coated with an alditol. In a further embodiment the invention relates to a powder mixture comprising a) calcium carbonate particles being at least partially coated with an alkali metal fluoride and b) particles of at least one alditol. Furthermore, the invention relates to a dry powder mixture comprising calcium carbonate particles and particles of at least one alditol. In these embodiments the calcium carbonate particles and the particles of at least one alditol have the same preferred features as described above with respect to the use of these particles and powder mixtures in dental powder blasting.

In the context of the present application the "dry" powder mixture is defined as a powder mixture which does not contain any water or other liquid (such as an oil) in addition to the moisture which is naturally present in the powder being in contact with the surrounding air.

Thus, the dry powder mixture of the present invention may still contain the amount of water which is present in equilibrium with the humidity of the surrounding air.

In a preferred embodiment the dry powder mixture of the present invention is free flowing. In particular, the dry powder mixture is not a paste like a tooth paste.

Finally, the present invention relates to a tooth cleaning method comprising the steps of: providing calcium carbonate particles as described above or a powder mixture as described above; and powder blasting a tooth surface with said particles or powder mixture.

In the method of the present invention, the particles or powder mixture are preferably mixed with air and water and the resulting mixture is applied onto the tooth surface to be treated by a powder-jet device that mixes the particles or powder mixture with air to form a powder/air mixture and blasts said powder/air mixture together with said water onto said tooth surface.

The present invention will now be explained in more detail by way of example, which is not intended to be construed as limiting.

EXAMPLES

Example 1

Calcium carbonate particles having a mean particle size of about 65 μm were coated with 1,500 ppm and 12,300 ppm sodium fluoride, respectively.

The thus obtained coated calcium carbonate particles were either used alone or in admixture with about 2 wt. % to about 6 wt. % of xylitol particles having a mean particle size in the range of 53 μm to 88 μm for powder blasting of tooth with a powder-jet device. Alternatively, the uncoated calcium carbonate particles were used in admixture with about 2 wt. % to about 6 wt. % of the xylitol particles.

By using the coated calcium carbonate particles alone or in admixture with the xylitol particles or by using the uncoated calcium carbonate particles in admixture with the xylitol particles the tooth was not only cleaned but at the same time remineralized.

Example 2

12 bovine teeth were divided in four groups of three. From each tooth, 4 surfaces of 2×2 mm were isolated from the buccal tooth surface. One surface of each tooth was held in artificial saliva and used as control. All remaining surfaces were etched using phosphoric acid gel.

The four groups of tooth surfaces were treated as follows:

Group 1: The enamel surfaces were immersed in 20 ml of artificial saliva containing 10% granulated Calcium Carbonate, for 24 hours.

Group 2: The enamel surfaces were immersed in 20 ml of artificial saliva containing 10% Air Flow Classic (Sodium Bicarbonate), for 24 hours.

Group 3: The enamel surfaces were immersed in 20 ml of artificial saliva containing 10% engineered Calcium Carbonate particles (Calcium Carbonate particles coated with Sodium Fluoride 1 wt. %), for 24 hours.

Group 4: The enamel surfaces were immersed in 20 ml of artificial saliva containing 10% engineered Calcium Carbonate particles (Calcium Carbonate particles coated with Sodium Fluoride 1 wt. % and Xylitol 10 wt. %), for 24 hours.

All samples were analyzed using SEM.

Figure 1B:
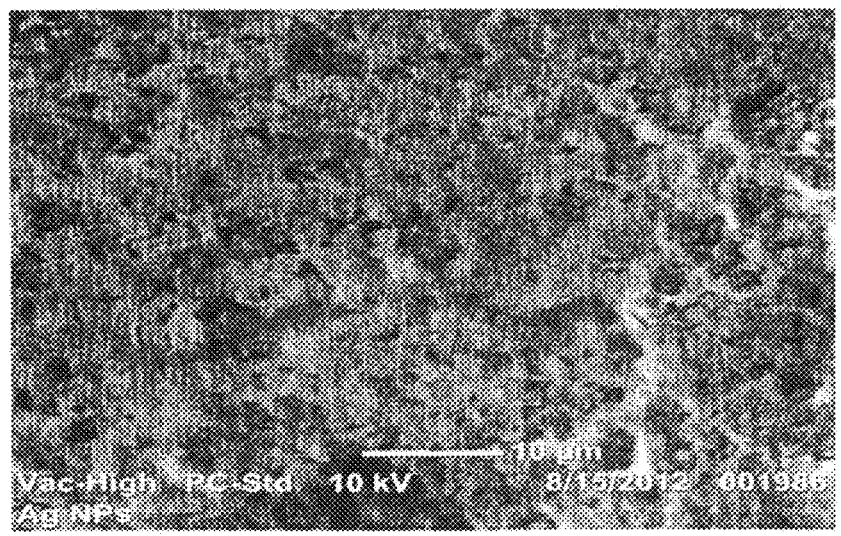
FIG. 1B is an image of the demineralized bovine enamel of FIG. 1A after treatment with calcium carbonate in accordance with Example 2 (Group 1).
Figure 2A:
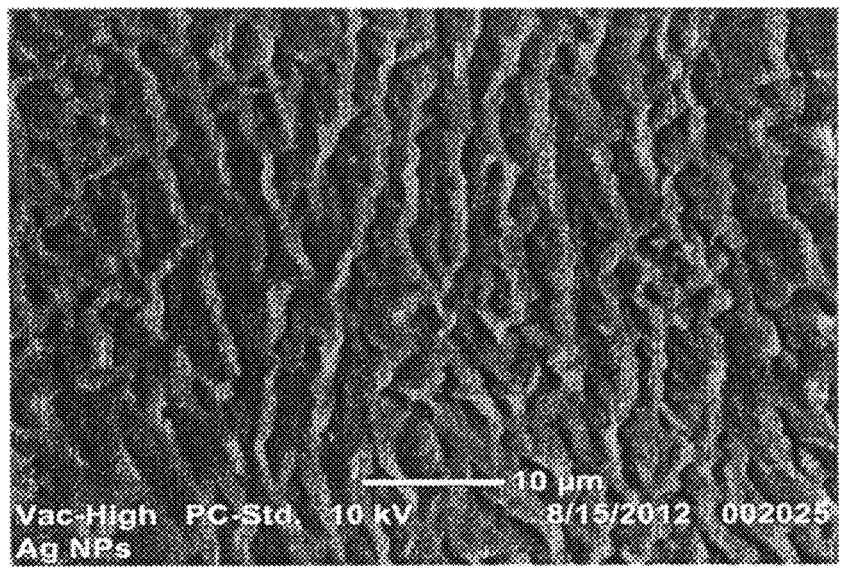
FIG. 2A is an image of demineralized bovine enamel before treatment with sodium bicarbonate in accordance with Example 2 (Group 2).
Figure 2B:
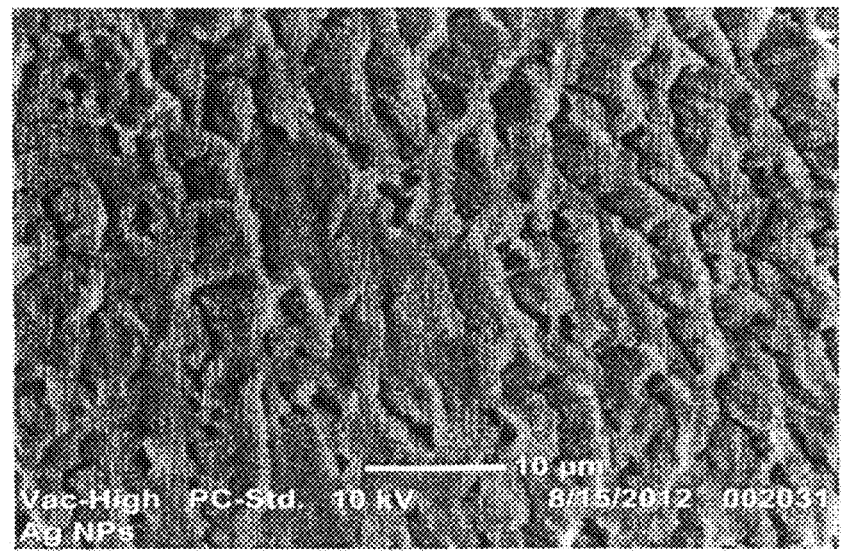
FIG. 2B is an image of the demineralized bovine enamel of FIG. 2A after treatment with sodium bicarbonate in accordance with Example 2 (Group 2).

Groups 1 and 2 are comparative examples conducted with calcium carbonate and sodium bicarbonate, respectively, as used in the prior art for dental powder blasting. Images of the enamel surfaces before and after treatment are presented in FIGS. 1A and 1B (Group 1) and 2A and 2B (Group 2). Both treatments show no remineralization. The fish scale structures of the enamel can still be seen, remineralization bridges were not observed.

Figure 3A:
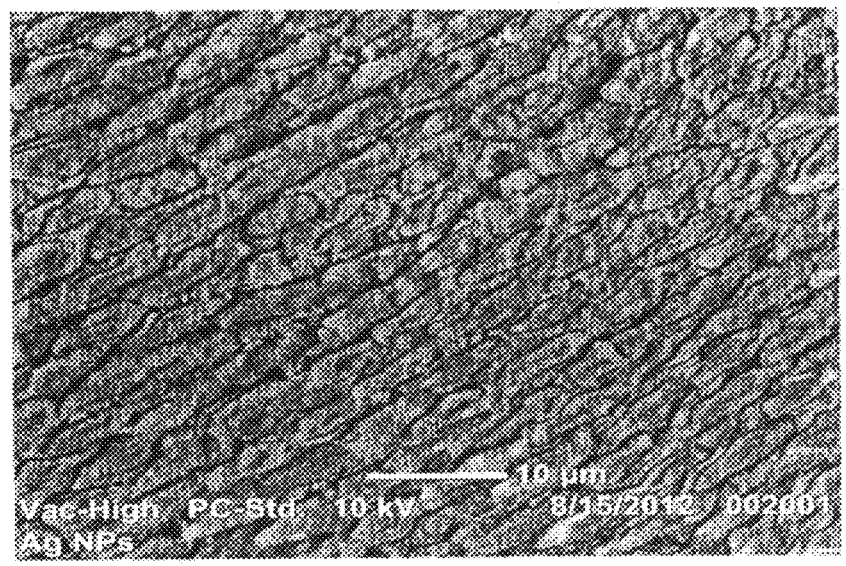
FIG. 3A is an image of demineralized bovine enamel with distinct structures before treatment with calcium carbonate particles coated with sodium fluoride 1 in accordance with Example 2 (Group 3).
Figure 3B:
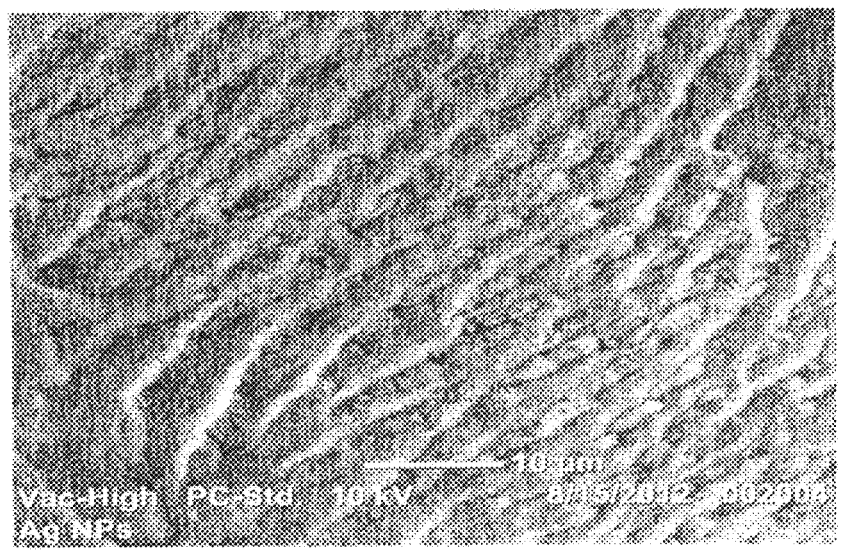
FIG. 3B is an image of the demineralized bovine enamel of FIG. 3A after treatment with calcium carbonate particles coated with sodium fluoride 1 in accordance with Example 2 (Group 3). It can be seen that bridges of precipitate start filling the gaps between the enamel structures.
Figure 4A:
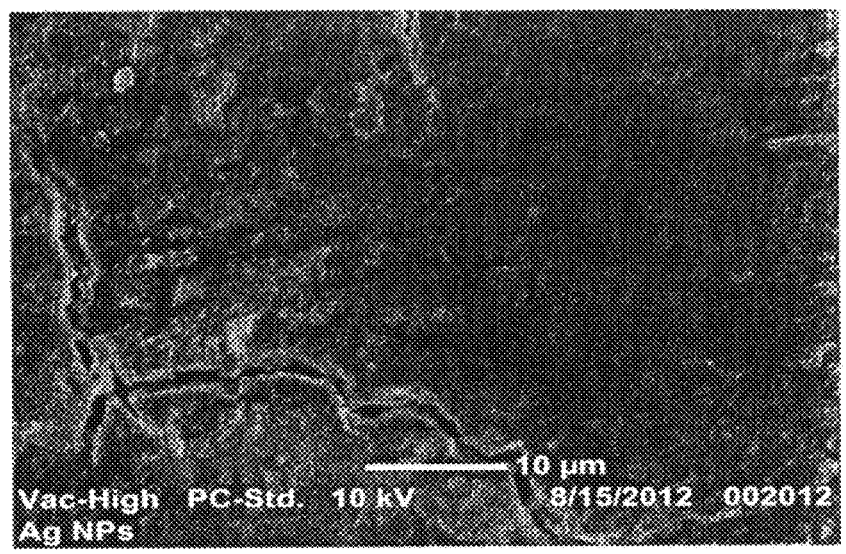
FIG. 4A is an image of demineralized bovine enamel before treatment with calcium carbonate particles spray coated with 1 wt. % of sodium fluoride and 10 wt. % of xylitol in accordance with Example 2 (Group 4).
Figure 4B:
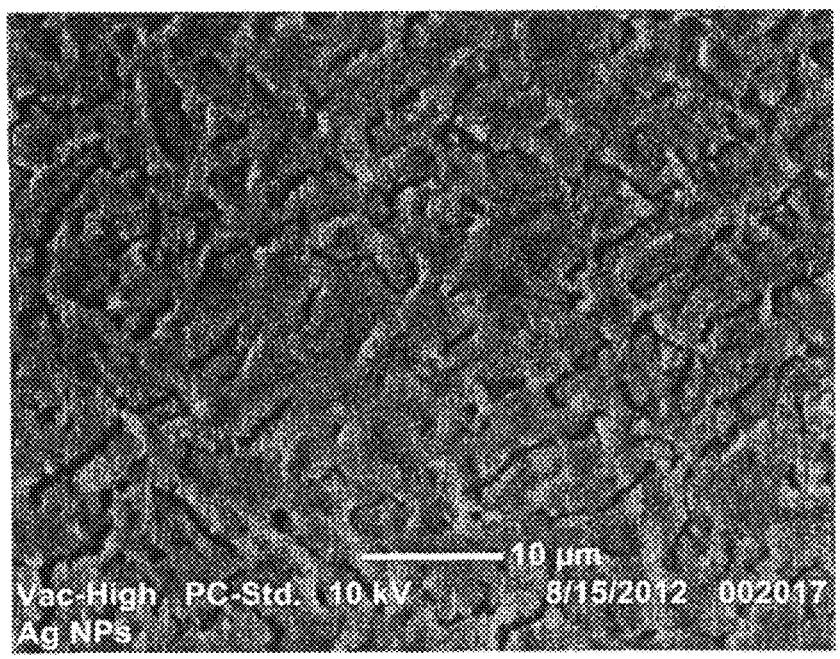
FIG. 4B is an image of the demineralized bovine enamel of FIG. 4A after treatment with calcium carbonate particles spray coated with 1 wt. % of sodium fluoride and 10 wt. % of xylitol in accordance with Example 2 (Group 4). The remineralization process is most evident. As can be seen in FIG. 4B, the treated enamel surfaces showed a build up of a uniform layer of precipitate, covering in most part the enamel structure.

Groups 3 and 4 are according to the invention using calcium carbonate particles coated with 1 wt. % of sodium fluoride in Group 3 and additionally with 10 wt. % of xylitol in Group 4. Images of the enamel surfaces before and after treatment are presented in FIGS. 3A and 3B (Group 3) and 4 (Group 4).

Example 3

Six human molars were scanned before and after demineralization with phosphoric acid, using a Canary Lab System (Quantum Dental Technologies).

The six molars were then treated as follows:

Molar 1 was immersed in 20 ml of artificial saliva containing 10% granulated Calcium Carbonate suspension, for 6 hours.

Molar 2 was immersed in 20 ml of artificial saliva containing 10% Air Flow Perio (Glycine), for 6 hours.

Molar 3 was immersed in 20 ml of artificial saliva containing 10% engineered Calcium Carbonate particles (Calcium Carbonate particles coated with Xylitol, 10 wt. %) for 6 hours.

Molar 4 was immersed in 20 ml of artificial saliva containing 10% engineered Calcium Carbonate particles (Calcium Carbonate particles coated with Sodium Fluoride 1 wt. %), for 6 hours.

Molar 5 was immersed in 20 ml of artificial saliva containing 10% engineered Calcium Carbonate particles (Calcium Carbonate particles coated with Sodium Fluoride 1 wt. % and Xylitol 10 wt. %), for 6 hours.

Molar 6 was immersed in 20 ml of artificial saliva containing 10% of a mixture of 88 wt. % Xylitol, 10 wt. % Calcium Carbonate granules, and 2 wt. % Silicon Dioxide, for 6 hours.

During the experiment, all samples were stored in 50 ml tubes, suspended in the solution using nylon line (to avoid direct contact with the precipitate) and maintained at 37° C. using a water bath.

The Canary Lab System measurements consisted on scanning a 2×2 mm area. The results of the measurements were reported in Canary Number and PTR Amplitude number. A decrease in the Canary Number represents an increase in the density of the enamel layer. A decrease in PTR Amplitude values represents an increase of thickness of the enamel layer.

The results are summarized in Tables 1 and 2 below.

TABLE 1

| Experiment | Canary Number before treatment | Canary Number after treatment | change in Canary Number | improvement vs. comparative Molar 1 |
|---|---|---|---|---|
| Molar 1 (comparative) | 17.50 | 21.73 | +24% | / |
| Molar 2 (comparative) | 18.09 | 22.62 | +25% | / |
| Molar 3 (invention) | 13.95 | 16.28 | +16% | 8% |
| Molar 4 (invention) | 21.12 | 18.45 | −14% | 38% |
| Molar 5 (invention) | 19.40 | 16.55 | −13% | 37% |
| Molar 6 (invention | 17.58 | 20.59 | +17% | 7% |

TABLE 2

| Experiment | PTR Amplitude before treatment | PTR Amplitude after treatment | change in PTR Amplitude | improvement vs. comparative Molar 1 |
|---|---|---|---|---|
| Molar 1 (comparative) | 76.9 | 106.0 | +38% | / |
| Molar 2 (comparative) | 77.6 | 101.4 | +31% | / |
| Molar 3 (invention) | 67.8 | 66.0 | −3% | 41% |
| Molar 4 (invention) | 114.6 | 116.0 | −1% | 39% |
| Molar 5 (invention) | 95.1 | 77.2 | −19% | 57% |
| Molar 6 (invention | 96.4 | 88.7 | −8% | 46% |

The data in the above Tables 1 and 2 confirm that treatment of human molar with the dental blasting powders according to the invention results in a significant decrease in the Canary Number and PTR Amplitude compared to the treatment with prior art blasting powders, in particular calcium carbonate. The decreases in Canary Number and PTR Amplitude demonstrate significant increases in density and thickness of the enamel layers.

The invention claimed is:

1. A combination tooth cleaning and remineralization method comprising the steps of:
    a. mixing by means of a powder-jet device (i) a dry powder comprising calcium carbonate particles that are at least partially coated with an alkali metal fluoride with (ii) air to form a powder/air mixture; and
    b. using said powder-jet device, powder blasting onto a tooth surface said powder/air mixture and water, wherein
    said powder/air mixture abrasively cleans said tooth surface; and
    said powder/air mixture and water form a slurry into which fluoride ion from said alkali metal fluoride is immediately released to thereby react with said calcium carbonate particles so as to enable remineralization of said tooth surface.

2. The method according to claim 1, wherein said alkali metal fluoride is sodium fluoride.

3. The method according to claim 2, wherein said calcium carbonate particles of step a have a mean particle size in the range of about 10 μm to about 200 μm.

4. The method according to claim 1, wherein the amount of said alkali metal fluoride coated onto said calcium carbonate particles in step a ranges from about 1,000 ppm to about 20,000 ppm relative to the weight of said calcium carbonate particles prior to coating.

5. The method according to claim 1, wherein said dry powder further contains from about 1 wt. % to about 20 wt. % of alditol based on the total weight of said dry powder.

6. The method according to claim 1, wherein said calcium carbonate particles of step a are at least partially coated with both said alkali metal fluoride and an alditol.

7. The method according to claim 6, wherein the alditol is xylitol.

8. The method according to claim 1, wherein said method further comprises performance of the following steps prior to step a: (i) spraying uncoated calcium carbonate particles with a solution containing said alkali metal fluoride and a solvent and then (ii) evaporating said solvent so as to generate said calcium carbonate particles that are at least partially coated with said alkali metal fluoride.

9. The combination tooth cleaning and remineralization method of claim 1, wherein said remineralization results in increased density and/or thickness of an enamel layer on said tooth.

* * * * *